US009139627B2

(12) United States Patent
Riebel

(10) Patent No.: US 9,139,627 B2
(45) Date of Patent: Sep. 22, 2015

(54) BIOPOLYMERS AND PROCESSES FOR MAKING SAME

(71) Applicant: GS Cleantech Corporation, New York, NY (US)

(72) Inventor: Michael J. Riebel, Mankato, MN (US)

(73) Assignee: GS CLEANTECH CORPORATION, New York, NY (US)

(*) Notice: Subject to any disclaimer, the term of this patent is extended or adjusted under 35 U.S.C. 154(b) by 258 days.

(21) Appl. No.: 13/768,732

(22) Filed: Feb. 15, 2013

(65) Prior Publication Data

US 2013/0206034 A1    Aug. 15, 2013

Related U.S. Application Data

(60) Provisional application No. 61/599,215, filed on Feb. 15, 2012, provisional application No. 61/614,862, filed on Mar. 23, 2012.

(51) Int. Cl.
| | |
|---|---|
| *C08L 97/02* | (2006.01) |
| *C12F 3/10* | (2006.01) |
| *C08H 99/00* | (2010.01) |
| *C07K 14/415* | (2006.01) |
| *C08B 37/00* | (2006.01) |
| *C09J 189/04* | (2006.01) |
| *B01D 1/18* | (2006.01) |
| *B01J 2/06* | (2006.01) |
| *C08J 11/04* | (2006.01) |
| *C08H 1/00* | (2006.01) |

(52) U.S. Cl.
CPC ............... *C07K 14/415* (2013.01); *B01D 1/18* (2013.01); *B01J 2/06* (2013.01); *C08B 37/00* (2013.01); *C08H 1/00* (2013.01); *C08H 99/00* (2013.01); *C08J 11/04* (2013.01); *C08L 97/02* (2013.01); *C09J 189/04* (2013.01); *C12F 3/10* (2013.01); *Y02E 50/17* (2013.01)

(58) Field of Classification Search
CPC ............ C12F 3/10; C08H 99/00; C08J 11/04; C08L 97/02
See application file for complete search history.

(56) References Cited

U.S. PATENT DOCUMENTS

| | | | |
|---|---|---|---|
| 3,959,511 | A | 5/1976 | Balaz et al. |
| 4,029,823 | A | 6/1977 | Bone et al. |
| 5,316,782 | A | 5/1994 | Zimlich, III |
| 5,439,701 | A | 8/1995 | Zimlich, III |
| 5,763,509 | A | 6/1998 | Eastin et al. |
| 5,997,939 | A | 12/1999 | Moechnig et al. |
| 6,710,128 | B1 | 3/2004 | Helmer et al. |
| 7,601,858 | B2 | 10/2009 | Cantrell et al. |
| 7,608,729 | B2 | 10/2009 | Winsness et al. |
| 7,618,660 | B2 | 11/2009 | Mohanty et al. |
| 7,625,961 | B2 | 12/2009 | Riebel et al. |
| 7,651,582 | B2 | 1/2010 | Weimer et al. |
| 7,937,850 | B2 * | 5/2011 | Tate et al. ......................... 34/191 |
| 8,008,516 | B2 | 8/2011 | Cantrell et al. |
| 8,008,517 | B2 | 8/2011 | Cantrell et al. |
| 8,168,037 | B2 | 5/2012 | Winsness et al. |
| 8,449,986 | B2 * | 5/2013 | Riebel et al. .................. 428/534 |
| 2004/0082044 | A1 | 4/2004 | Prevost et al. |
| 2005/0017214 | A1 | 1/2005 | Hartley et al. |
| 2005/0019545 | A1 | 1/2005 | Riebel |
| 2005/0040251 | A1 | 2/2005 | Daly |
| 2006/0093726 | A1 | 5/2006 | Bachmeier et al. |
| 2006/0147582 | A1 | 7/2006 | Riebel |
| 2007/0238891 | A1 | 10/2007 | Winsness et al. |
| 2008/0110577 | A1 | 5/2008 | Winsness |
| 2008/0131947 | A1 | 6/2008 | Wicking |
| 2008/0190567 | A1 | 8/2008 | Winsness |
| 2008/0202684 | A1 | 8/2008 | Weimer et al. |

(Continued)

FOREIGN PATENT DOCUMENTS

WO    2008030854 A2    3/2008

OTHER PUBLICATIONS

Hu, C et al: "Thermoplastics from acetylated zein-and-oil-free corn distillers dried grains with solubles", Biomass and Bioenergy, Pergamon Amsterdam, NL, vol. 35, No. 2, Feb. 1, 2011; pp. 884-892, XP027578823, (SSN: 0961-9534, DOI: 10.1016/J.BIOMBIOE.2010.11.006) (retrived on Dec. 29, 2010).
Zarrinbakhsh et al: "Biodegradable Green Composites from Distiller's Dried Grains with Solubles (DDGS) and a Polyhydroxy (butyrate-co-valerate) (PHBV)-Based Bioplastic", Macromol. Mater. Eng. 2011, 296, 1035-1045.
International Search Report & Written Opinion issued in International Application No. PCT/US2013/026445, dated Jun. 21, 2013; 12 pages.
"Using Dried Distillers Grains to Make Bioadhesive", May 24, 2010, pp. 1-2; XP055066350: Retrieved from the Internet: URL:http://www.michiganagconnection.com/story-state.php?ID=386&yr=2010 [retreived on Jun. 12, 2013].

(Continued)

*Primary Examiner* — David M Brunsman
(74) *Attorney, Agent, or Firm* — Cantor Colburn LLP

(57) ABSTRACT

A dried distiller soluble based biopolymer, processes for forming the biopolymer, and articles of manufacture thereof. The produced dried distillers solubles derives from co-products of corn fermentation facilities and is comprised in part of water-soluble proteins. A biopolymer consists essentially of dried distillers solubles, and an article of manufacture includes a biopolymer consisting of dried distillers solubles and an optional additive. The process of forming dried distiller solubles involves separating whole stillage into a liquid fraction and a solid fraction, wherein the liquid fraction comprises water soluble proteins in an amount greater than the solid fraction, and wherein the solid fraction has a higher solid content than the liquid fraction. The liquid fraction is sprayed at an elevated temperature to remove at least a portion of moisture in the liquid fraction and form particles and granules of the liquid fraction. Addition moisture is removed from the particles and granules in a fluidized bed to form dried distillers solubles, wherein the particles and granules are heated to a temperature less than 300° F. and have a residence time effective to reduce the moisture content of the dried distillers solubles to less than 20 percent to greater than 3 percent by weight.

15 Claims, 1 Drawing Sheet

(56) References Cited

U.S. PATENT DOCUMENTS

| | | | |
|---|---|---|---|
| 2008/0299632 A1 | 12/2008 | Winsness et al. | |
| 2009/0226571 A1 | 9/2009 | Freyer et al. | |
| 2009/0259060 A1 | 10/2009 | Cantrell et al. | |
| 2009/0269477 A1* | 10/2009 | Tate et al. | 426/656 |
| 2009/0281203 A1* | 11/2009 | Riebel et al. | 521/44 |
| 2010/0028484 A1 | 2/2010 | Kriesler et al. | |
| 2010/0082312 A1 | 4/2010 | Macharia et al. | |
| 2010/0224711 A1 | 9/2010 | Kreisler et al. | |
| 2011/0282085 A1 | 11/2011 | Cantrell et al. | |
| 2012/0009658 A1 | 1/2012 | Winsness | |
| 2012/0199531 A1 | 8/2012 | Winsness | |
| 2012/0205324 A1 | 8/2012 | Cantrell et al. | |
| 2013/0078349 A1 | 3/2013 | Newman | |
| 2013/0149758 A1 | 6/2013 | Medoff et al. | |
| 2013/0206034 A1 | 8/2013 | Riebel | |
| 2013/0206342 A1 | 8/2013 | Dahmes et al. | |

OTHER PUBLICATIONS

International Search Report and Written Opinion issued in International Application No. PCT/US2013/026440 dated Sep. 20, 2013; 19 pages.

Li et al: "Adhevise Performance of Sorghum Protein Extracted from Sorghum DDGS and Flour", Journal of Polymers and the Environment; Formerlu: 'Journal of Environmental Polymer Degradation', Kluwer Academic Publishers-Plenum Publishers, NE, vol. 19, No. 3, Jun. 1, 2011, pp. 755-765.

Hu, et al; "Thermoplastics from Acetylated Zein-and-Oil-Free Corn Distillers Dried Grains with Solubles", Biomass and Bioenergy, Pergamon, Amsterdam, NL. vol. 35, No. 2; Feb. 1, 2011, pp. 884-892, XP027578823, ISSN: 0961-9534; DOI.

International Search Report issued in International Application No. PCT/US2013/026445, dated Jun. 21, 2013; 5 pages.

Written Opinion of the International Searching Authority issued in International Application No. PCT/US2013/026445, dated Jun. 21, 2013; 7 pages.

Zarrinbakhsh, et al; "Biodegradable Green composites from Distiller's Dried Grains with Solubles (DDGS) and a Polyhydroxy (butyrate-co-valerate) (PHBV)-Based Bioplastic", Macromolecular materials and Engineering, vol. 296, No. 11, Nov. 10, 2011; pp. 1035-1045, XP0550566377. ISSN: 1438-7492, DOI.

Notification Concerning Transmittal of International Preliminary Report on Patentability (Chapter I of the Patent Cooperation Treaty), issued in International Application PCT/US2013/026440, dated Aug. 28, 2014; 12 pages.

Notification Concerning Transmittal of International Preliminary Report on Patentability (Chapter I of the Patent Cooperation Treaty), issued in International Application PCT/US2013/026445, dated Aug. 28, 2014; 8 pages.

International Search Report and Written Opinion, issued in International Application No. PCT/US2013/026452, mailed on Jun. 7, 2013; 10 pages.

\* cited by examiner

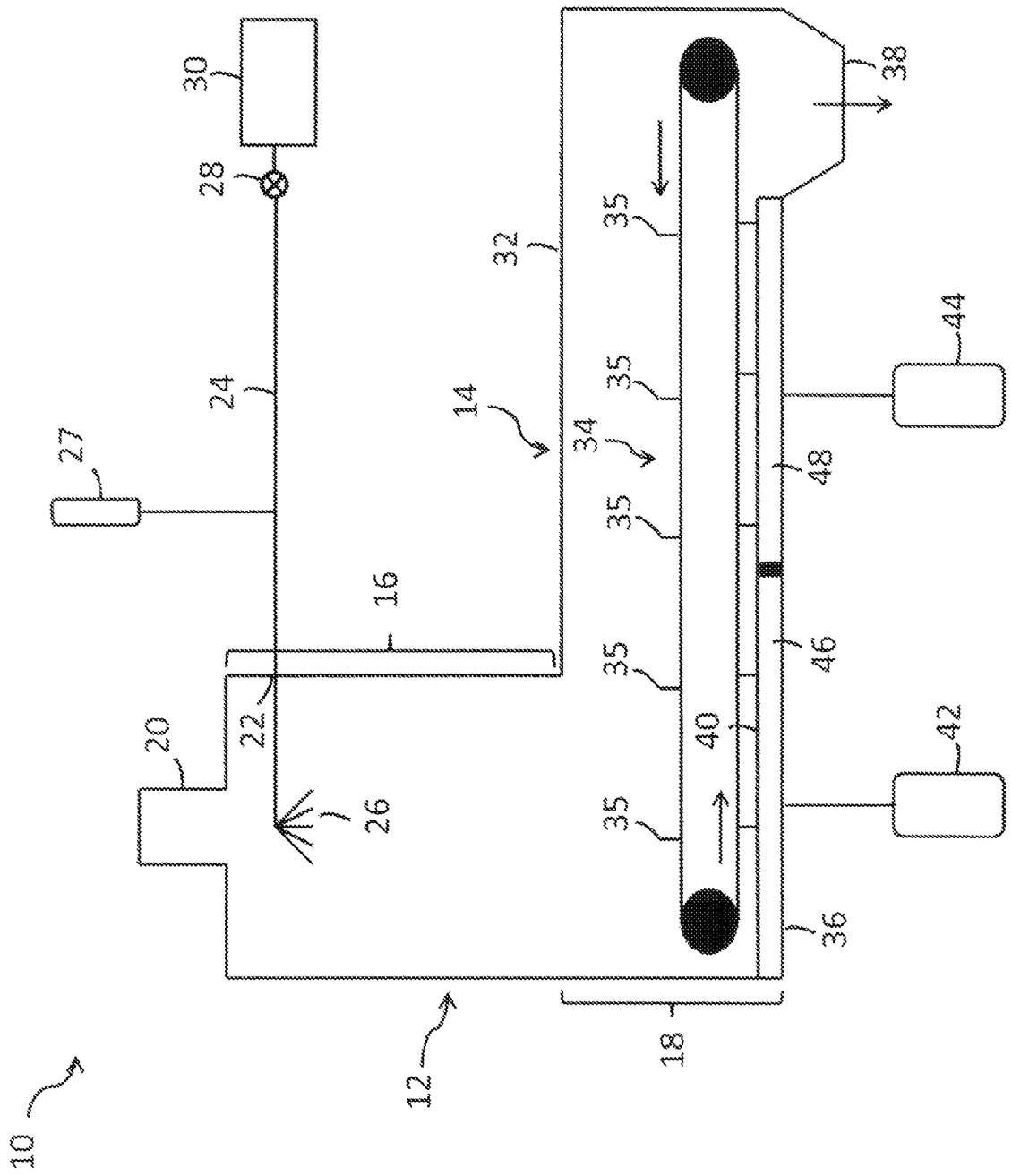

BIOPOLYMERS AND PROCESSES FOR MAKING SAME

CROSS REFERENCE TO RELATED APPLICATIONS

This application claims priority to and the benefit of the U.S. Provisional Patent Application Nos. 61/599,215, filed on Feb. 15, 2012 and 61/614,862 filed Mar. 23, 2012, which are fully incorporated herein by reference.

BACKGROUND

The present disclosure generally relates to biopolymers, processes for making the biopolymers, and articles of manufacturing. More particularly, the present disclosure relates to biopolymers formed from dried distillers solubles produced in the corn fermentation process.

Because of its relatively low investment and operational requirements, dry milling has become the primary method for converting starch within corn to ethanol. In the dry milling process, corn is first screened and ground to a flour. The resulting flour is combined with water and the starch within the corn is conventionally hydrolyzed into sugar by liquefaction and saccharification. The mixture is then fermented with yeast to convert the sugar into ethanol and carbon dioxide. About 30% of the mass of each kernel of corn accepted by corn ethanol producers is converted into ethanol in this manner. The output of fermentation, a mixture of ethanol, water, protein, carbohydrates, fat, minerals, solids and other unfermented components, is then distilled to boil off ethanol for recovery, purification and sale, leaving the remainder of the mixture in the bottom of the distillation stage.

The remainder at the bottom of the distillation stage is referred to as whole stillage (WS) and is typically subjected to a press or centrifugation process to separate the coarse solids from the liquid. The liquid fraction is commonly referred to as distillers solubles or thin stillage (TS). TS is frequently concentrated in an evaporator to become condensed distillers solubles (CDS), which is also commonly referred to as syrup. The coarse solids, or wet cake, collected from the centrifuge or press are known as wet distillers grains (WDG). Drying the WDG produces dried distillers grains (DDG). The WDG can be combined with the CDS to form what is commonly referred to as wet distillers grains with solubles (WDGS), which can then be dried to form dried distillers grains with solubles (DDGS). The DDG or DDGS typically has a moisture content less than 15% by weight.

In some instances, the CDS is subjected to a high temperature drying process to form dried distillers solubles, which reportedly has been used as a thermoplastic additive with a metal oxide and fiber in the preparation of extruded articles.

In other instances, the partially concentrated thin stillage or condensed distillers solubles, prior to being combined with the wet distillers grains, is subjected to a corn oil extraction process to remove at least a portion of the oil contained therein. The extracted crude corn oil can be used as a feedstock for the production of biodiesel and other products. The remaining condensed distillers solubles with at least a portion of the oil removed is then typically combined with the wet distillers grains to form WDGS and further dried as DDGS for use as animal feed. Exemplary corn oil extraction processes are disclosed in U.S. Pat. Nos. 7,601,858, 7,608,729, 8,008, 516, and 8,008,517, all of which are incorporated by reference in their entireties.

The corn fermentation solids have been used to form biopolymer compositions. As noted above, the solid fraction includes the portion of solids deriving from the whole stillage. For example, U.S. Pat. No. 7,625,961 to Riebel discloses compositions that generally include the fermentation solids at 0.1 to 95% by weight and a thermoactive material at 0.1 to 95% by weight. The thermoactive material is selected to have a melting point less than the fermentation solid and generally serves as a binder in which the fermentation material can be embedded. Exemplary thermoactive materials include thermoplastics, thermoset materials, resins and the like. The fermentation solids disclosed by Riebel are generally selected from the group consisting of fermented protein solid, distiller's dried grain, distiller's dried grain-200, distiller's dried corn, distiller's dried fractionated corn, distiller's dried starch root crop, distiller's dried tuber, distiller's dried root, distiller's dried cereal grain, distiller's dried wheat, distiller's dried rye, distiller's dried rice, distiller's dried millet, distiller's dried oats, distiller's dried potato, wet cake, and solvent washed wet cake.

The liquid fraction, which contains water soluble components such as water soluble protein, may be further processed, e.g., concentration, oil extraction, and the like. The liquid fraction is then typically added back to the DDG to form DDGS, i.e., dried distillers grains with solubles.

Thus, it would be desirable for a more robust renewable material. Accordingly, it is to solving this and other needs the present disclosure is directed.

BRIEF SUMMARY

Disclosed herein are biopolymers formed from dried distiller solubles, processes for making the same, articles of manufacture, and an apparatus suitable for making the dried distillers solubles. In one embodiment, a biopolymer consists essentially of dried distillers solubles. Dried distillers solubles can be in a powder or granular form.

In another embodiment, an article of manufacture comprises a biopolymer consisting essentially of dried distillers solubles.

The disclosure may be understood more readily by reference to the following detailed description of the various features of the disclosure and the examples included therein.

BRIEF DESCRIPTION OF THE DRAWINGS

Referring now to the FIGURE wherein the like elements are numbered alike:

The FIGURE illustrates an exemplary drying apparatus for forming the dried distillers solubles in accordance with the present disclosure.

DETAILED DESCRIPTION

The present disclosure is generally directed to dried distillers solubles (DDS) based biopolymers, processes for making the same, and articles of manufacture. As used herein, the DDS is obtained from a specific byproduct feedstream resulting from fermentation of biomass such as corn to produce whole stillage. As noted above, the byproduct of fermentation, i.e., whole stillage, is generally separated into a solids fraction and a liquid fraction. It is the liquid fraction, also referred to as thin stillage, which is used to form the DDS.

The solids fraction, also referred to as the wet cake or wet distillers grains (WDG), is generally utilized to form the dried distillers grains (DDG), which has a markedly different composition than that of DDS. For example, the CDS precursor to DDS includes water soluble components such as water soluble proteins that form the basis of the biopolymer properties whereas the WDG fraction generally lacks such soluble constituents.

Advantageously, the biopolymers formed from the DDS are elastomeric, biodegradable, and can be made without the need for additional binders. Further, the DDS are subjected to a multistep low temperature drying process to form particles and granules. This low temperature process provides DDS in a powder and/or granular form with a moisture content of about 3% to about 20% by weight, and in other embodiments, about 5% to about 12% by weight. The biopolymers and articles of manufacture produced therefrom can be formed entirely from the DDS as may be desired for some applications. The DDS can be kneaded by various mechanical means as desired. Optionally, the DDS can be admixed with various other components depending on the intended application.

In one embodiment, prior to its use as a biopolymer, the DDS is first subjected to an oil extraction process that removes at least a portion of the oil contained therein. The particular oil extraction process is not intended to be limited and can occur at any stage of the process for forming the DDS. For example, the whole stillage, thin stillage, concentrated thin stillage (also referred to as condensed distillers solubles or CDS), or the DDS itself may be subjected to an oil extraction process. Exemplary oil extraction processes are disclosed in U.S. Pat. No. 8,168,037 to Winsness et al., incorporated herein by reference in its entirety.

The DDS materials derive exclusively from co-products of fermentation and, as noted above, can be comprised of water-soluble proteins, among other constituents. The use of DDS obtained from the liquid fraction overcomes many of the problems noted in the prior art as it relates to biopolymers in general and as it relates to the prior art's use of dried distillers grains with or without solubles, i.e., DDG or DDGS. Moreover, because of the uniqueness of the DDS, the properties can be readily manipulated by additives and/or by compositional changes as a function of processing. With regard to compositional changes, because the DDS is ultimately obtained from whole stillage (i.e., the residue remaining after ethanol distillation), it should be apparent that modification, physical or chemical, of the final biopolymer properties can be made to any one of the product streams upstream from the DDS as well as on the DDS itself. In another embodiment, the upstream treatment can include the removal or partial removal of starch or carbohydrates that remain in the non-fermented byproduct of the corn-to-ethanol fermentation process. These methods can include but are not limited to $CO_2$ extraction, an additional fermentation step, etc. Furthermore the upstream treatment can include filtration, membrane filtration or centrifugation technologies to isolate and reduce additional components within such as but not limited to suspended or selected dissolved solids.

The DDS resultant material by itself is generally in a powder and/or granular form and, in some embodiments, can be used neat as the biopolymer. For example, heat and pressure can be used to form a profiled article of manufacture using DDS as a stand alone material. By way of example, the DDS in the polymer and/or granular form can be extruded with a single or twin screw extruder, for example, to form a profiled article of manufacture. Alternatively, the biopolymer can be compounded with other polymers and/or monomers to tailor the desired properties of the biopolymer blend to the desired end use. Still further, the DDS biopolymer can be functionalized directly or upstream in the process of making the DDS, wherein the particular functionalization is selected based on the desired properties of the article of manufacture.

The resultant DDS material can also be used as a resin extender, wherein the DDS is blended with another polymer to lower its cost and provide various functional advantages in the final blend.

The process for forming the DDS generally includes separating the whole stillage into a solids fraction and a liquids fraction; and drying the liquid fraction, i.e., thin stillage or CDS, to form the DDS. In the corn fermentation process, the liquid fraction that is first obtained after distillation and after separation of the whole stillage residue, i.e., the thin stillage feedstream, is typically first fed to an evaporator, e.g., a multistage evaporator, to remove a portion of the water contained therein to produce condensed distillers solubles (CDS), also referred to by those in the art as thin stillage concentrate. In ethanol production facilities, the evaporation temperatures for the evaporators are typically about 100 to 230° F. and more typically about 110 to 200° F. The CDS is then fed to a drying apparatus to form the DDS. However, in some embodiments, it may be desirable to form the DDS directly from the thin stillage. In such embodiments, or where CDS is first formed by evaporation of the thin stillage, it may be desirable in some applications to remove at least a portion of the oil, water and/or other constituents contained therein prior to drying to form the DDS. The amount of oil and/or other constituents removed can be used to tailor the biopolymer properties. In addition to the production of DDS and its subsequent use as a biopolymer, the extracted corn oil itself can be used for various applications including, but not limited to, production of biodiesel, thereby transforming what was previously considered as a low value product into a significant revenue stream for ethanol plant operator.

Once a portion of the oil is removed from the CDS, in some applications it may be desired to further concentrate the CDS and subject this further concentrated CDS to an additional oil or water extraction process to remove additional oil or water. Alternatively, this concentrated CDS material may be dried in a drier apparatus to produce the DDS. Again, doing so can be used to manipulate the final biopolymer properties as may be desired for different applications.

The drying process applied to the liquid fraction generally includes a fluidized bed apparatus configured to heat CDS (or thin stillage) to a temperature less than 300° F. in most embodiments, less than 250° F. in other embodiments, and less than 200° F. in still other embodiments. In one embodiment, the process generally includes spraying or conducting CDS through one or more nozzles and subjecting the resultant output to a flow of heated gases within a chamber to evaporate at least a portion of the moisture from the CDS and form discrete particles and granules. The discrete particles and granules are then carried from the chamber by means of a fluidized bed to facilitate additional drying and/or cooling that may include additional moisture removal. The fluidized bed includes a perforated surface in fluid communication with a fluidizing medium. The bed may include a single or plurality of zones, where the first zone introduces a heated inert fluidizing medium and additional zones facilitates cooling of the particles and/or granules prior to discharge from the apparatus. An exemplary apparatus is provided in the FIGURE. The perforated surface of the fluidized bed can be a fixed bed, perforated moving conveyor, a perforated vibrating bed, a vibrating perforated moving conveyor or other.

Referring now to the FIGURE, the exemplary fluidized bed apparatus generally designated by reference numeral 10 includes an atomization section 12 and a fluidized bed section 14. The atomization section 12 includes an elongated housing having a top portion 16 and a bottom portion 18. The bottom portion 18 is fluidly connected to the fluidized bed section 14.

The top portion 16 includes an exhaust conduit 20 generally positioned to carry exhaust gases from the atomization section 12. The exhaust gases, which may be at an elevated temperature and may contain vaporized water, solvent and/or other residuals, may be further treated or discharged to the atmosphere, or the thermal energy contained therein may be used in additional thermal processes. For example, the exhaust could be fed to a heat exchanger to minimize the energy requirements associated with operating the fluidized beds, the ethanol production facility, and the like. Optionally, air adjusted weirs and/or baffles (not shown) can be additionally incorporated to manage residence times.

The atomization section 12 further includes at least one inlet 22 for introducing CDS 30 into the drying chamber via conduit 24. The inlet 22 is fluidly connected to an atomization nozzle 26 for atomizing the CDS 30 within the drying chamber. A source of compressed gas 27 is in fluid communication with the atomization nozzle 26. The compressed gas can be fed into conduit 24 or may be separately provided via a separate conduit to the atomization nozzle 26. A positive displacement pump 28 may be employed to pump the CDS 30 to the atomization nozzle 26. The CDS 30 source may be plumbed directly from the fermentation facility, e.g., following evaporation, or may be stored within a holding tank as may be desired for some applications.

The fluidized bed section 14 includes an elongated housing 32 having an opening in fluid communication with the drying chamber. A horizontally disposed conveyor belt 34 may be used and if so, is seated within the fluidized bed section 14. In one embodiment, the conveyor belt 34 further include drag bars 35 spaced apart on a surface thereof in operative communication with a fluidized bed 14 such that as the conveyor belt 34 rotates, the drag bars 35 push the DDS (dried CDS) to a discharge end 38.

The discharge end 38 can be configured for product collection or may be configured to provide the discharged material back to the drying chamber or the fluid bed section.

The fluidized bed 36 includes a perforated top surface 40 a non-perforated bottom surface and sidewalls extending therefrom to the perforated top surface 40. The fluidized bed 35 is in fluid communication with one or more inert fluidized mediums, two of which are shown, e.g., 42, 44. The bed includes at least one zone, two of which are shown: zones 46, and 48. Zone 46 is distally positioned from the discharge outlet and provides a fluidized medium to the particles and granules carried by the conveyor belt 34 or moving perforated bed. The zone 48 is proximate to the discharge outlet and provides inert fluidized medium that is generally at a temperature less than the first zone but in some embodiments it may be desired to be to cooler. Each additional zone intermediate zone 48 and the discharge outlet 38 can be configured to provide a reduced temperature relative to an adjacent zone so that the particles and granules are at about room temperature upon discharge from the discharge outlet 38 as may be desired for some facilities. Optionally, the fluid bed zone(s) may be configured to provide cooling, wherein the predominant drying of CDS can occur in the atomization section. In another embodiment, the perforated surface 40 is a belt conveyor such that it conveys the pressure sensitive material while drying and/or cooling the particles and granules. There may be multiple zones within this conveyor and sealing surfaces or close tolerances within to minimize the air loss between the moving perforated conveyor, the side walls and/or the zone(s).

The apparatus 10 can be operated in batch or continuous fashion, and can incorporate one or more devices for accomplishing thermal treatment apart or in combination with that discussed above, e.g., convection, conduction and/or radiation, in sequence and/or concurrently. Likewise, the inert drying gases and fluidized bed mediums can be metered to precisely control intermediate temperature, residence time and other relevant process variables such that, for example, moisture is removed while avoiding undesirable particle deformation or reactions.

In one embodiment, the drying process is configured to provide the DDS in a powder and/or granular form with a moisture content of about 3 to about 20% by weight, and in other embodiments, about 5 to about 12% by weight. The material can then be kneaded by various mechanical means as may be desired, e.g., roller mills, mixing mills, and extrusion processing. The DDS is elastomeric and partially or fully water soluble absent addition of additional additives, e.g., crosslinkers, vulcanizing agents, and the like. The various additives can be added by wet mixing prior to the drying process or dry mixing with the kneaded material.

In other embodiments, one or more of the sources such as thin stillage, thin stillage concentrate, partially de-oiled thin stillage or partially de-oiled thin stillage concentrate can be homogenized by subjecting the source to high shear. Shear can be produced through the use of a high pressure pump and a fixed or adjustable orifice but other devices can be used to create the same effect as will be appreciated by those skilled in the art. This process advantageously aides in milling the insoluble fractions to a smaller size as well as creating uniform product. In another embodiment, the residual starch and other carbohydrates that were not converted to ethanol and remain in the byproduct feed stream can be removed using known techniques such as $CO_2$ extraction, an additional fermentation step, and the like.

Advantageously, the drying apparatus provides a much less thermally aggressive environment for drying the CDS to form DDS granules. As previously discussed, DDS is obtained from the liquid fraction of the separated whole stillage. Relative to the solids fraction, i.e., wet cake or wet distiller grains, the liquid fraction contains a significantly higher percentage of water soluble components, e.g., water soluble proteins. Condensed distillers solubles generally are more than 20% dissolved solids and less than 80% suspended solids. In other embodiments, the percentage of dissolved solids in the CDS is more than 40% of the total solids in the CDS/DDS stream. In still other embodiments, the percentage of dissolved solids in the CDS is more than 60% of the total solids in the CDS/DDS stream.

Constituent proteins and carbohydrates can form insoluble compounds (Maillard or browning products) when exposed to high temperatures in the presence of moisture. Moreover, glutelin, which comprises about 40% of the protein in corn, are known to form disulfide bonds and crosslink with themselves and other proteins at elevated temperatures, a result that can be attributed to oxidation of constituent sulfhydryl groups to disulfides. The functionality of the DDS can also be impaired with too much heat, for example, by unwanted denaturation. Such outcomes can be decreased or avoided by minimizing and controlling the application of heat in the manner of the present invention.

Alternatively, the drying apparatus may be configured to supplement the convective processes with conductive processes, such as by incorporating an induction heater or intercooler into the base of a fluid bed. Emissive methods can also be incorporated, such as by adding infrared energy emitters into the housing walls, or by adding a zone in which the feed material is treated by electromagnetic radiation at wavelengths, intensities and times sufficient to gently heat the interior of particles to enable more efficient, lower temperature convection while avoiding excessive surface dehydration and degradation, or other adverse reactions that could impair functionality.

By way of a further example, any of the foregoing thermal treatment methods could optionally involve introduction of one or more additives, which may include liquid feedstream or any co-product from a prior or subsequent stage of this invention or the fermentation facility, during any stage of thermal treatment to regulate the characteristics as desired to, for example, prevent degradation or otherwise render the resulting DDS suitable for further processing and/or its anticipated end use.

The thermal treatment processes described above may also be utilized to facilitate targeted reactions, such as functionalization, polymerization, crosslinking and the like, as may be necessary to condition the DDS for its intended end use.

The CDS without oil extraction or with at least a portion of the oil (i.e., fat) removed can be dried in the fluidized bed drying apparatus to form the DDS. Table 1 provides a general comparison on a dry matter basis of a CDS composition without oil extraction and a CDS composition with at least a portion of the oil removed (referred to as "CDS-F"). Reference to CDS-F is not intended to infer that oil is completely removed from the dried distillers solubles. In some embodiments, it may be beneficial to subject the CDS to multiple oil and/or water extraction steps to further decrease and manipulate the amount of oil and/or water contained in the DDS product material. In most embodiments, the oil content in the DDS product material is from 3 to 15% by weight although higher or lower amounts of oil may be desired in certain applications

TABLE 1

|  | CDS | CDS-F |
| --- | --- | --- |
| Protein (%) | 18 | 21 |
| Fat (%) | 20 | 7 |
| Carbohydrates (%) | 48 | 56 |
| Ash (%) | 14 | 16 |
| Total (%) | 100 | 100 |

As demonstrated in Table 1, the amount of oil can easily be varied.

In a similar manner, the other constituents defining the DDS composition can be varied. For example, thin stillage or CDS can be treated to remove a portion of the carbohydrates and/or a portion of the low molecular weight proteins. Alternatively, the DDS can be treated to modify one or more of the constituents within the composition. For example, the proteins and/or carbohydrates can be functionalized with different materials to provide further manipulation of the biopolymer properties. By way of example, protein modifications can include, for example, treating proteins with an acid, base or other agent that alters the structure of one or more of the amino acid side chains, which, in turn, alters the character of the protein and/or amino acids. The net charge carried by protein molecules is of significance presently since it affects the behavior and functionality of the molecules. For example, the high glutamine content of prolamines provides a means for manipulating the charge characteristics of the protein by deamidation, thereby providing a wide range of hydrophobicity. In one embodiment, deamidation involves mild acid catalyzed deamidation at a pH of about 1 at temperatures from about 25° C. to about 65° C. for a period of time sufficient to accomplish the desired level of deamidation. In some embodiments, acids that form stable dispersions and are useful within these classes include, without limitation, lactic acid, citric acid, malonic acid, phosphoric acid, fumaric acid, maleic acid, maleic anhydride, maleated propylenes, glutaric acid, transaconitic acid, acetic acid, propionic acid, sorbic acid, cysteine and glycyl glycine. In one embodiment, lactic acid in the form of polylactic acid is used. In another embodiment, maleated propylenes, such as G-3003 and G-3015 manufactured by Eastman chemicals are used.

The thin stillage and CDS feedstreams have conventionally been viewed as low-value by-products, i.e., waste products. Problematically, the chemical and physical characteristics of CDS adversely affect (and dilute the value of) wet distillers grains when combined therewith. The resulting product stream, i.e., the precursor to DDGS, has reduced protein content and is stickier and less tolerant to spoilage than it would be without addition of CDS following evaporation. Consequently, producers have to burn more fossil fuel-derived natural gas to dry DDGS longer than would otherwise be required in order to vaporize more water and to avoid handling and spoilage issues. Low moisture content translates directly into extended storage life. Producers have generally had little choice but to follow the standard industry practice of combining CDS with wet distillers grains (WDG) prior to drying for the want of an economically and technically feasible alternative. An aspect of this disclosure is to provide such an alternative and empower producers to reduce these inefficiencies by diverting and separately processing CDS. As a result, the WDG does not require the extended drying times since spoilage as a function of moisture content is less of a concern.

Thin stillage and its more concentrated CDS form are generally comprised of water, protein, fat, carbohydrates, ash, and relatively minor amounts of other fermentation byproducts. At least some of the protein in the feedstream has been hydrolyzed as a function of the fermentation process conditions and is water-soluble. The fat (oil) is substantially comprised of glycerides and is present in a free, bound and/or emulsified state. The carbohydrate fraction is further comprised of various sugars, partially-hydrolyzed starch, and insoluble polysaccharides (cellulose, hemicellulose and lignin). Ash includes residual minerals. Fermentation byproducts include glycerol, lactic acid, acetic acid, yeast, and the like.

By the time CDS exits the evaporators, its protein and other constituents have changed significantly due to continuous treatment during the fermentation process with hot water, enzymes, caustic, acid, urea and/or other chemicals, at times under pressure and/or vacuum, for more than two days. Many of these process conditions are severe and are generally known to facilitate at least some degree of hydrolysis, denaturation and other presently favorable reactions and reactants.

By way of example, ethanol facilities using the method taught by Winsness in U.S. patent application Ser. No. 11/908,891 incorporated herein by reference in its entirety, iteratively wash the whole stillage with at least a portion of the thin stillage after initial separation of whole stillage into wet distillers grains and thin stillage. This step increases the content of lower density, low molecular weight and soluble components in the thin stillage to enhance derivative co-product value, e.g., DDS. Moreover, as disclosed by Winsness, fat removal efficiencies can be optionally increased by chemical addition and/or by increasing temperature and/or concentrated thin stillage or CDS residence time at targeted temperatures. Using such methods, CDS might be held at an elevated temperature for an extended period of time at a pH of, for example, 3.5 to 4.5, before removing at least some fat (oil) and directing the CDS for final evaporation.

The DDS or any of the upstream intermediate product feedstreams including, but not limited to, whole stillage, thin stillage, condensed distillers solubles, defatted condensed distillers soluble, and the like, can comprise at least another component, to manipulate the properties of the biopolymer such as, but not limited to, improving and/or controlling the viscosity, shelf-life, and stability. Non-limiting examples of additional components include tackifiers, plasticizers (plasticizing oils or extender oils), waxes, antioxidants, UV stabilizers, colorants or pigments, fillers, flow aids, biocides, lubricants, water, oil, coupling agents, crosslinking agents, surfactants, catalysts solvents, hydrolyzing agents, and combinations thereof.

In further embodiments, the DDS and/or DDS derivative or any of the upstream product feedstreams disclosed herein optionally can comprise or incorporate a plasticizer or plasticizing oil or an extender oil that may reduce viscosity and/or improve extrusion properties. Any plasticizer known to a person of ordinary skill in the art may be used in the adhesion composition disclosed herein. Non-limiting examples of plasticizers include olefin oligomers, low molecular weight polyolefins such as liquid polybutene, phthalates, mineral oils such as naphthenic, paraffinic, or hydrogenated (white) oils (e.g. Kaydol oil), vegetable and animal oil and their derivatives, petroleum derived oils, and combinations thereof. In some embodiments, the plasticizers include polypropylene, po lybutene, hydrogenated po lyisoprene, hydrogenated polybutadiene, polypiperylene and copolymers of piperylene and isoprene, and the like having average molecular weights between about 350 and about 10,000. In other embodiments, the plasticizers include glyceryl esters of the usual fatty acids and polymerization products thereof.

In some embodiments, a suitable insoluble plasticizer may be selected from the group which includes dipropylene glycol dibenzoate, pentaerythritol tetrabenzoate; polyethylene glycol 400-di-2-ethylhexoate; 2-ethylhexyl diphenyl phsophate; butyl benzyl phthalate, dibutyl phthalate, dioctyl phthalate, various substituted citrates, and glycerates.

In further embodiments, the DDS and/or DDS derivative or any of the upstream product feedstreams disclosed herein optionally can comprise a wax that may reduce the melt viscosity in addition to reducing costs. Any wax known to a person of ordinary skill in the art can be used in the adhesion composition disclosed herein. Non-limiting examples of suitable waxes include petroleum waxes, polyolefin waxes such as low molecular weight polyethylene or polypropylene, synthetic waxes, paraffin and microcrystalline waxes having melting points from about 55 to about 110° C., Fischer-Tropsch waxes and combinations thereof. In some embodiments, the wax is a low molecular weight polyethylene homopolymer or interpolymer having a number average molecular weight of about 400 to about 6,000 g/mole.

In further embodiments, the DDS and/or DDS derivative or any of the upstream product feedstreams disclosed herein optionally can comprise an antioxidant or a stabilizer. Any antioxidant known to a person of ordinary skill in the art may be used in the adhesion composition disclosed herein. Non-limiting examples of suitable antioxidants include amine-based antioxidants such as alkyl diphenylamines, phenyl-α-naphthylamine, alkyl or aralkyl substituted phenyl-α-naphthylamine, alkylated p-phenylene diamines, tetramethyl-diaminodiphenylamine and the like; and hindered phenol compounds such as 2,6-di-t-butyl-4-methylphenol; 1,3,5-trimethyl-2,4,6-tris(3',5'-di-t-butyl-4'-hydroxybenzyl)benzene; tetrakis(methylene(3,5-di-t-butyl-4-hydroxyhydrocinnamate)]methane (e.g., IRGANOX™ 1010, from Ciba Geigy, N.Y.); octadecyl-3,5-di-t-butyl-4-hydroxycinnamate (e.g., IRGANOX™ 1076, commercially available from Ciba Geigy) and combinations thereof.

In further embodiments, the DDS and/or DDS derivative or any of the upstream product feedstreams disclosed herein optionally can comprise an UV stabilizer that may prevent or reduce the degradation of the compositions by UV radiation. Any UV stabilizer known to a person of ordinary skill in the art may be used in the adhesion composition disclosed herein. Non-limiting examples of suitable UV stabilizers include benzophenones, benzotriazoles, aryl esters, oxanilides, acrylic esters, formamidine, carbon black, hindered amines, nickel quenchers, hindered amines, phenolic antioxidants, metallic salts, zinc compounds and combinations thereof.

In further embodiments, the DDS and/or DDS derivative or any of the upstream product feedstreams disclosed herein optionally can comprise a colorant or pigment. Any colorant or pigment known to a person of ordinary skill in the art may be used in the adhesion composition disclosed herein. Non-limiting examples of suitable colorants or pigments include inorganic pigments such as titanium dioxide and carbon black, phthalocyanine pigments, and other organic pigments.

In further embodiments, the DDS and/or DDS derivative or any of the upstream product feedstreams disclosed herein optionally can comprise a filler. Any filler known to a person of ordinary skill in the art may be used in the adhesion composition disclosed herein. Non-limiting examples of suitable fillers include sand, talc, dolomite, calcium carbonate, clay, silica, mica, wollastonite, feldspar, aluminum silicate, alumina, hydrated alumina, glass bead, glass microsphere, ceramic microsphere, thermoplastic microsphere, barite, wood flour, magnesium carbonate, calcium hydroxide, calcium oxide, magnesium oxide, aluminum oxide, silicon oxide, iron oxide, boron nitride, titanium oxide, talc, pyrophyllite clay, silicate pigment, polishing powder, mica, sericite, bentonite, pearlite, zeolite, fluorite, dolomite, quick lime, slaked lime, kaolin, chlorite, diatomaceous earth, soda ash, and combinations thereof.

In further embodiments, the DDS and/or DDS derivative or any of the upstream product feedstreams disclosed herein optionally can comprise a catalyst. Suitable catalysts include without limitation, metallic catalysts and non-metallic catalysts. Metal catalysts include, without limitation, metal oxides, including, for example, zinc oxide, titanium dioxide, copper oxides, (cuprous oxide and/or cupric oxide), aluminum oxide, calcium oxide, stannous oxide, lead oxide and other metal oxides; and metals, for example, zinc, titanium, copper, iron, nickel, zirconium, and aluminum. Other catalysts include, without limitation, fly ash and Portland cement.

Some oxides also assist with odor reduction and increase the shelf life. Without being bound by theory, oxides, such as titanium dioxide, may reduce auto-oxidation.

In some embodiments, the DDS and/or DDS derivative or any of the upstream product feedstreams disclosed herein optionally can comprise a vulcanizing agent. Suitable vulcanizing agents include sulfur, zinc oxides, MDI urethanes, and the like.

In further embodiments, the DDS and/or DDS derivative or any of the upstream product feedstreams disclosed herein optionally can comprise a crosslinker Crosslinking agents also have the ability to increase the mechanical and physical performance of the present biopolymer. As used herein, crosslinking generally refers to linking at least two polymer chains comprised, for example, of proteins, peptides, polysaccharides, and/or synthetic polymers of the corn protein material.

Suitable crosslinking agents include one or more of metallic salts (e.g., NaCl or rock salt) and salt hydrates (which may improve mechanical properties), urea, formaldehyde, urea-formaldehyde, polyesters, phenol and phenolic resins, melamine, methyl diisocyanide (MDI), polymeric methyl diphenyl diisocyanate (pMDI), polymeric hexamethylene diisocyanate (pHMDI), amine-epichlorohydrin adducts, epoxides, zinc sulfate, aldehydes and urea-aldehyde resins epoxides, aldehyde, aldehyde starch, dialdehyde starch, glyoxal, urea glyoxal, urea-aldehyde, polyamine epichlorohydrin resin, polyamidoamine-epichlorohydrin resin, polyalkylene polyamine-epichlorohydrin, amine polymer-epichlorohydrin resin epoxy, resin mixtures, combinations thereof, and the like. The same or similar agents may also serve as binders.

The amine-epichlorohydrin adducts are defined as those prepared through the reaction of epichlorohydrin with amine-functional compounds. Among these are polyamidoamine-epichlorohydrin resins (PAE resins), polyalkylenepolyamine-epichlorohydrin (PAPAE resins) and amine polymer-epichlorohydrin resins (APE resins). The PAE resins include secondary amine-based azetidinium-functional PAE resins, tertiary amine polyamide-based epoxide-functional resins and tertiary amine polyamidourylene-based epoxide-functional PAE resins. It is also possible to use low molecular weight amine-epichlorohydrin condensates.

Additional additives can include a fiber additive. Suitable fibers include any of a variety of natural and synthetic fibers. Cellulose fibers include, without limitation, those from wood, agricultural fibers, including flax, hemp, kenaf, wheat, soybean, switchgrass, and grass, fibers obtained from paper and other fiber recycling, including, without limitation, household and industrial paper recycling streams, fibrous waste from the paper or wood industries, including paper mill sludge. Synthetic fibers include fiberglass, Kevlar, carbon fiber, nylon; mixtures or combinations thereof, and the like. Mineral or silica additives may also be used. The fiber can modify the performance of the biopolymers. For example, longer fibers can be added to impart higher flexural and rupture modulus to the cured or dried biopolymer.

Nanomaterials may also be used as fillers, including Nano-Cell (LDI Composites), which is a blend of cellulose, minerals and clay that has been processed into a submicron material. It is derived from paper mill sludge. NanoCell also contains small percentages of metals and titanium dioxide. Other forms of nanomaterials, such as nanofibers, nanotubes, nanocellulosics, nanoclays and other forms of nanomaterials may also be included in the DDS biocomposite additive and/or the biopolymer.

Other materials that can include components found in latex paint, including, without limitation, latex compounds, including, without limitation, acrylic latexes such as styrenated acrylic latex; calcium carbonate, colorants, dispersants, such as, for example, napthalene sulfonic acid condensation products; ammonium hydroxide; surfactants; glycol ethers, including (propylene glycol) methyl ether; 2,2,4-trimethylpentanediol-1,3-monoisobutyrate; sodium nitrite; ethylene glycols, such as triethylene glycol bis(2-ethylhexanoate); drying agents, such as metal oxides, including, without limitation, zirconium oxides, cobalt oxides and iron oxides, as well as ethylene oxides and ethylene oxide derivatives and condensates, including, without limitation, fatty alcohol ethoxylate, alkylphenol ethoxylate, fatty acid ethoxylate, ethoxylated fatty amines, and the like; preservatives, emulsifiers and thickeners.

Additional additives include citric acid including citric acid monohydrate contains many carboxyl groups that are expected to interact with both proteins and cellulosic based materials at elevated temperatures.

The DDS can also be dry blended with a wide range of additional powder resin as a bioextender to either lower the cost of the petrochemical resin powder or provide functional advantages to the overall blend. DDS can also be added to various formaldehyde resins wherein the proteins can scavenge the residual formaldehyde and increase the biobased content of the resulting product. Such powder or liquid resins include but not limited to: phenol formaldehyde, urea formaldehyde and melamine formaldehyde adhesives.

As noted above, the DDS after being subjected to the drying process is in powder and/or granular form. The resulting DDS is elastomeric and can be injection molded to extruded to form a stable profiled article of manufacture. The particular end use for the article of manufacture is not intended to be limited. For example, flat sheets can be readily formed or profiled structures can be formed. Advantageously, low temperature extrusion processes, typically less than 200° F., can be used to form various products such as, for example, baseboards, edgebanding, and other flexible profiles.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A biopolymer consisting essentially of dried distillers solubles free of starch and/or carbohydrates.

2. The biopolymer of claim 1, wherein the dried distillers solubles comprises modified water soluble proteins.

3. The biopolymer of claim 1, wherein the dried distillers solubles has a moisture content of about 3 to about 20% by weight.

4. The biopolymer of claim 3, wherein the dried distillers solubles has a moisture content of about 5 to about 12% by weight.

5. The biopolymer of claim 1, wherein the dried distillers solubles is a corn-to-ethanol fermentation byproduct.

6. The biopolymer of claim 1, wherein the dried distillers solubles is in a powder or a granular form.

7. The biopolymer of claim 1, wherein the dried distillers solubles comprises functionalized proteins.

8. An article of manufacture, comprising:
a biopolymer consisting essentially of dried distillers solubles free of starch and/or carbohydrates.

9. The article of manufacture of claim 8, wherein the biopolymer is extruded to form a shape defining the article of manufacture.

10. The article of manufacture of claim 8, wherein the biopolymer and at least one additional component are extruded to form a shape defining the article of manufacture.

11. The article of manufacture of claim 10, wherein the at least one additional component comprises a polymer.

12. The article of manufacture of claim 10, wherein the at least one additional component comprises a crosslinker selected from metallic salts, salt hydrates, urea, formaldehyde, polyesters, amine-epichlorohydrin adducts, epoxides, or any combination thereof.

13. The article of manufacture of claim 10, wherein the at least one additional component comprises a metal oxide selected from zinc oxide, titanium dioxide, cuprous oxide, cupric oxide, aluminum oxide, calcium oxide, stannous oxide, lead oxide, or any combination thereof.

14. The article of manufacture of claim 10, wherein the at least one additional component comprises a filler selected from sand, talc, clay, silica, mica, magnesium oxide, mica, silicon dioxide, kaolin, iron oxide, nanomaterials, or any combination thereof.

15. The article of manufacture of claim 10, wherein the at least one additional component comprises a vulcanizing agent.

* * * * *